US010420831B2

(12) United States Patent
Wu et al.

(10) Patent No.: US 10,420,831 B2
(45) Date of Patent: Sep. 24, 2019

(54) INACTIVATION OF VIRUSES BY DELIPIDATION

(71) Applicant: ELI LILLY AND COMPANY, Indianapolis, IN (US)

(72) Inventors: Stephen Wu, Fishers, IN (US); Leyla Diaz, Indianapolis, IN (US)

(73) Assignee: Elanco US Inc., Greenfield, IN (US)

( * ) Notice: Subject to any disclaimer, the term of this patent is extended or adjusted under 35 U.S.C. 154(b) by 0 days.

(21) Appl. No.: 16/060,561

(22) PCT Filed: Jan. 20, 2017

(86) PCT No.: PCT/US2017/014267
§ 371 (c)(1),
(2) Date: Jun. 8, 2018

(87) PCT Pub. No.: WO2017/132059
PCT Pub. Date: Aug. 3, 2017

(65) Prior Publication Data
US 2018/0360945 A1 Dec. 20, 2018

Related U.S. Application Data

(60) Provisional application No. 62/287,488, filed on Jan. 27, 2016.

(51) Int. Cl.
| C07D 487/04 | (2006.01) |
| A61K 31/519 | (2006.01) |
| A61K 31/5377 | (2006.01) |
| A61K 39/12 | (2006.01) |
| A61K 45/06 | (2006.01) |
| C12N 7/00 | (2006.01) |
| A61K 39/00 | (2006.01) |

(52) U.S. Cl.
CPC .............. *A61K 39/12* (2013.01); *C12N 7/00* (2013.01); *A61K 2039/5252* (2013.01); *A61K 2039/552* (2013.01); *C12N 2760/16134* (2013.01); *C12N 2760/16151* (2013.01); *C12N 2770/10051* (2013.01)

(58) Field of Classification Search
CPC .. A61K 2300/00; A61K 31/724; A61K 33/40; A61K 38/44; A61K 45/06
See application file for complete search history.

(56) References Cited

U.S. PATENT DOCUMENTS

| 6,306,401 B1 | 10/2001 | Brown et al. |
| 7,407,662 B2 | 8/2008 | Cham et al. |
| 8,506,968 B2 | 8/2013 | Akeefe et al. |
| 8,613,934 B2 | 12/2013 | Raviv et al. |
| 8,629,101 B2 | 1/2014 | Pessi et al. |
| 2004/0202676 A1 | 10/2004 | Rubido et al. |

OTHER PUBLICATIONS

Sun, Xiangjie and Gary R. Whittaker, "Role for Influenza Virus Envelope Cholesterol in Virus Entry and Infection", Journal of Virology, Dec. 2003, pp. 12543-12551, vol. 77, No. 23, American Society for Microbiology.

Vishwanathan, Sundaram A., et al., "Large Changes in the CRAC Segment of gp41 of HIV Do Not Destroy Fusion Activity if the Segment Interacts with Cholesterol", Biochemistry, 2008, 47, pp. 11869-11876, American Chemical Society.

Lorizate, Maier, et al., "Recognition and Blocking of HIV-1 gp41 Pre-transmembrane Sequence by Monoclonal 4E10 Antibody in a Raft-like Membrane Environment", Journal of Biological Chemistry, Dec. 22, 2006, vol. 281, No. 51, pp. 39598-39606, The American Society for Biochemistry and Molecular Biology, Inc.

Vyas, Girish N., et al., "Derivation of non-infectious envelope proteins from virions isolated from plasma negative for HIV antibodies", Elsevier Ltd on behalf of the International Alliance for Biological Standardization, Biologicals, 2012, vol. 40, pp. 15-20.

Huarte, Nerea, et al., "Lipid modulation of membrane-bound epitope recognition and blocking by HIV-1 neutralizing antibodies", Federation of European Biochemical Societies, 2008, Elsevier B.V., vol. 582, pp. 3798-3804.

Moore, NF., et al., "Interaction of vesicular stomatitis virus with lipid vesicles: depletion of cholesterol and effect on virion membrane fluidity and infectivity.", Journal of Virology, Aug. 1978, vol. 27, No. 2, pp. 320-329, American Society of Microbiology.

Pal, Ranajit, et al., "Alteration of the Membrane Lipid Composition and Infectivity of Vesicular Stomatitis Virus by Growth in a Chinese Hamster Ovary Cell Sterol Mutant and in Lipid-supplemented Baby Hamster Kidney Clone 21 Cells", The Journal of Biological Chemistry, vol. 255, No. 16, 1980, pp. 7688-7693.

Pal, Ranajit, et al., "Depletion and Exchange of Cholesterol from the Membrane of Vesicular Stomatitis Virus by Interaction with Serum Lipoproteins or Poly(vinylpyrrolidone) Complexed with Bovine Serum Albumin", American Chemical Society, Biochemistry, 1981, vol. 20, No. 3, pp. 530-539.

Wharton, S.A., et al., "Membrane Fusion by Peptide Analogues of Influenza Virus Haemagglutinin", J. gen. Virol., National Institute of Medical Research, 1988, vol. 69, pp. 1847-1857.

Lu, Xiongbin, et al., "Asymmetric Requirement for Cholesterol in Receptor-Bearing but Not Envelope-Bearing Membranes for Fusion Mediated by Ecotropic Murine Leukemia Virus", Journal of Virology, 2002, vol. 76, No. 13, pp. 6701-6709.

Graham, David R.M, et al., "Cholesterol Depletion of Human Immunodeficiency Virus Type 1 and Simian Immunodeficiency Virus with β-Cyclodextrin Inactivates and Permeabilizes the Virions: Evidence for Virion-Association Lipid Rafts", Journal of Virology, American Society of Microbiology, 2003, vol. 77, No. 15, pp. 8237-8248.

(Continued)

*Primary Examiner* — Barry A Chestnut
(74) *Attorney, Agent, or Firm* — David L Pflugh

(57) ABSTRACT

The present invention relates to vaccines containing enveloped viruses whose envelopes have been depleted of lipids using methyl β-cyclodextrin (MBCD). Delipidation of enveloped viruses in a two-step process abolishes the infectivity of those viruses, which allows delipidated viruses to be used safely in vaccines. Use of MBCD to deplete lipids such as cholesterol, in contrast to other methods, results in viruses with less than 20% of the cholesterol of an untreated virus but such delipidated viruses retain at least 85% of the protein content of an untreated virus. Delipidation by MBCD also preserves the immunogenicity of the viral proteins. The present invention of using MBCD treatment in a two-step process to delipidate enveloped virus represents a new alternative for generation of inactivated viruses which are incorporated into effective vaccines.

16 Claims, No Drawings

(56) References Cited

OTHER PUBLICATIONS

Beer, Christiane, et al., "The temperature stability of mouse retroviruses depends on the cholesterol levels of viral lipid shell and cellular plasma membrane", Journal of Virology, 2003, vol. 308, pp. 137-146.

Imhoff, Heidi, et al., "Canine Distemper Virus Infection Requires Cholesterol in the Viral Envelope", Journal of Virology, American Society for Microbiology, 2007, vol. 81, No. 8, pp. 4158-4165.

Ren, Xiaofeng, et al., "Importance of cholesterol for infection of cells by transmissible gastroenteritis virus", Elsevier, Virus Research, vol. 137, 2008, pp. 220-224.

Funk, Anneke, et al., "Duck Hepatitis B Virus Requires Cholesterol for Endosomal Escape during Virus Entry", American Society for Microbiology, Journal of Virology, 2008, vol. 82, No. 21, pp. 10532-10542.

Wang, W., et al., "Lipid rafts play an important role in the vesicular stomatitis virus life cycle", Springer-Verlag, Arch Virol, 2009, vol. 154, pp. 595-600.

Zhu, Liqian, et al., "Critical role of cholesterol in bovine herpesvirus type 1 infection of MDBK cells", Elsevier, Veterinary Microbiology, 2010, vol. 144, pp. 51-57.

Fujita, Hiroshi, et al., "Methyl-beta cyclodextrin alters the production and infectivity of Sendai virus", Springer-Verlag, Arch Virol, 2011, vol. 156, pp. 995-1005.

Sousa, Ivanildo P., et al., "Envelope Lipid-packing as a Critical Factor for the Biological Activity and Stability of Alphavirus Particles Isolated from Mammalian and Mosquito Cells", The Journal of Biological Chemistry, vol. 286, No. 3, pp. 1730-1736, 2011, The American Society for Biochemistry and Molecular Biology, Inc.

Ren, Xiaofeng, et al., "Cholesterol Dependence of Pseudorabies Herpesvirus Entry", Springer, Curr Microbiol, 2011, vol. 62, pp. 261-266.

Tang, Yuyang, et al., "Cholesterol Depletion Inactivates XMRV and Leads to Viral Envelope Protein Release from Virions: Evidence for Role of Cholesterol in XMRV Infection", Plos One, 2012, vol. 7, Issue 10, pp. 1-11.

Lai, Alex L., et al., "Fusion Activity of HIV gp41 Fusion Domain Is Related to Its Secondary Structure and Depth of Membrane Insertion in a Cholesterol-Dependent Fashion", Elsevier, Journal of Molecular Biology, 2012, vol. 418, pp. 3-15.

Carro, Ana C and Elsa Damonte, "Requirement of cholesterol in the viral envelope for dengue virus infection", Elsevier, Virus Research, 2013, vol. 174, pp. 78-87.

Liu, Su-Yang and Denis Gerlier, et al., "Interferon-Inducible Cholesterol-25-Hydroxylase Broadly Inhibits Viral Entry by Production of 25-Hydroxycholesterol", Elsevier, Inc., Immunity, 2013, vol. 38, pp. 92-105.

Chazal, Nathalie, et al., "Virus Entry, Assembly, Budding, and Membrane Rafts", American Society for Microbiology, Microbiology and Molecular Biology Reviews, 2003, vol. 67, No. 2, pp. 226-237.

Waheed, Abdul A and Eric O. Freed, et al., "The Role of Lipids in Retrovirus Replication", Viruses, 2010, vol. 2, pp. 1146-1180, ISSN 1999-4915.

Lorizate, Maier, et al., "Role of Lipids in Virus Replication", Cold Spring Harbor Perspectives in Biology, 2011, pp. 1-20.

Van Meer, Gerrit, et al., "Membrane lipids: where they are and how they behave", National Institutes of Health, Nat Rev Mol Cell Biol. 2008, vol. 9, No. 2, pp. 1-28.

Ridsdale, Andrew, et al., "Cholesterol Is Required for Efficient Endoplasmic Reticulum-to-Golgi Transport of Secretory Membrane Proteins", The American Society for Cell Biology, Molecular Biology of the Cell, 2006, vol. 17, pp. 1593-1605.

Zidovetzki, Raphael, et al., "Use of cyclodextrins to manipulate plasma membrane cholesterol content: evidence, misconceptions and control strategies", National Institutes of Health, Biochim Biophysys Acta, 2007, 1768(6), 1311-1324, pp. 1-27.

Sun, Ying, et al., "Cellular membrane cholesterol is required for porcine reproductive and respiratory syndrome virus entry and release in MARC-145 cells", Science China, Life Sciences, 2011, vol. 54, No. 11:1011-1018.

Mackenzie, Jason M., et al., "Cholesterol Manipulation by West Nile Virus Perturbs the Cellular Immune Response", Elsevier Inc., Cell Host & Microbe, 2007, vol. 2, pp. 229-239.

Veit, Michael, et al., "Association of Influenza Virus Proteins with Membrane Rafts", Hindawi Publishing Corporation, Advances in Virology, 2011, Article ID 370606, pp. 1-14.

Iwasaki, Akiko, et al., "Innate immunity to influenza virus infection", Nature Reviews, Immunology, 2014, vol. 14, pp. 315-328.

Koyama, Shohei, et al., "Innate immune response to viral infection", Elsevier, ScienceDirect, Cytokine 43, 2008, pp. 336-341.

Das, Akash, et al., "Three pools of plasma membrane cholesterol and their relation to cholesterol homeostasis", eLife, Biochemistry Cell biology, 2014, DOI: 10.7554/eLife.02882.

Paul, MD, William E., et al., "Fundamental Immunology", Seventh Edition, Wolters Kluwer Lippincott Williams & Wilkins, ISBN 98-1-4511-1783-7.

Lauring, Adam S., et al., "Rationalizing the development of live attenuated virus vaccines", Nat Biotechnol, Jun. 2010; vol. 28, No. 6, pp. 573-579.

Gerl, Mathias J., et al., "Quantitative analysis of the lipidomes of the influenza virus envelope and MDCK cell apical membrane", The Journal of Cell Biology, The Rockefeller University Press, vol. 196, No. 2, pp. 213-221.

Fields, M.D., Bernard N., et al., Fields Virology, Third Edition, Lippincott Williams & Wilkins, vol. 1, ISBN 0-7817-02534-4.

Cham, B. E., K. Vickery, R. Tohidi-Esfahani, and Y. Cossart. "Delipidation of a hepadnavirus: Viral inactivation and vaccine development." Journal of virological methods 137, No. 1 (2006): 160-163.

Kalyana Sundaram, Ramalingam Venkat, Huiyuan Li, Lauren Bailey, Adel A. Rashad, Rachna Aneja, Karl Weiss, James Huynh et al. "Impact of HIV-1 membrane cholesterol on cell-independent lytic inactivation and cellular infectivity." Biochemistry 55, No. 3 (2016): 447-458.

INACTIVATION OF VIRUSES BY DELIPIDATION

This application claims priority to PCT Application Number PCT/US2017/014267, filed Feb. 14, 2017 and published in English as WO2017/132059 on Aug. 3, 2017, which claims priority to U.S. Provisional Application No. 62/287,488 filed Jan. 27, 2016.

The present invention relates to vaccines containing enveloped viral particles, whose envelopes have been delipidated using methyl β-cyclodextrin (MBCD).

A virus is a mobile genetic element which has no metabolic activity on its own. Instead, a virus must infect a host cell and use that host cell's energy and processes in order to reproduce. Some viruses are "naked," which means an individual viral particle, or virion, is comprised only of the capsid surrounding the viral genome and perhaps a few virally-encoded nonstructural proteins. In other viruses, the capsid is contained within a membrane or envelope. Because the viral genome is generally too small to encode proteins involved in lipid synthesis, such enveloped viruses must construct their envelopes from the host cell lipids. The lipid content of a viral envelope thus varies depending on the lipid characteristics of the host cell.

Viruses are well-adapted to their host organisms and are often pathogenic, causing disease and even death to their hosts. Viruses can have a large economic impact, either by infecting humans and/or their companion animals, or by affecting plants and animals which are a source of food. Vaccines are the preferred method of protecting a host animal from viral infection. A vaccine creates protective immune responses to viruses comprising antibodies and cellular immunity. Both types of responses are often required to reduce new infections of host cells and to clear viral particles and infected cells from the host.

Nearly 40 years ago, Moore et al. (J. Virol. 27(2): 320-329, 1978) demonstrated using cholesterol-free vesicles that depletion of cholesterol from viral envelopes could reduce the ability of viral particles to infect their target cells. In contrast, other investigators reported viral infectivity required the presence of cholesterol in the target cell membrane but not in the viral envelope. Still others have postulated that the process of removing cholesterol, rather than the lack of cholesterol in the envelopes, is the cause of decreased infectivity. Regardless of the role of cholesterol in virus function, complete and permanent loss of infectivity has not been demonstrated for cholesterol-depleted viruses, nor have cholesterol-depleted viruses been shown to be useful in safe and effective vaccines.

Chemical means of depleting cholesterol have been reported, such as, for example, the use of cyclodextrins, n-butanol, di-isopropyl ether (DIPE), fluoroether such as sevoflurane, surfactants such as TRITON X-100™ (polyethylene glycol p-(1,1,3,3-tetramethylbutyl)-phenyl ether or polyoxyethylene octyl phenyl ether) or TWEEN 20™ (PEG (20) sorbitan monolaurate), diethyl ether, and combinations thereof. Some chemical means have proved too harsh, resulting in the loss of viral proteins from the virions or in structural changes to the remaining proteins. The presence and native conformation of the proteins would be necessary in order for cholesterol-depleted virions to be useful in vaccines, particularly vaccines which stimulate the production of neutralizing antibodies directed to viral envelope proteins.

In some cases, depletion of cholesterol has been shown to be reversible. Addition of exogenous cholesterol could reconstitute the viral envelope and restore infectivity. This could pose a safety concern regarding the use of cholesterol-depleted viruses in vaccines, as cholesterol and other lipids present in the blood or other bodily fluids, or even host cell membranes coming in contact with cholesterol-depleted virions, could potentially reconstitute the virions and restore infectivity.

Vaccines containing attenuated viruses are usually considered to be the most effective at generating protective immunity. However, there is a safety concern that the attenuated viruses could mutate or recombine and thus revert to a virulent state. Inactivated (i.e. killed) viruses are usually considered to be safer for use in vaccines, but the means of inactivation often alters or destroys antigenic epitopes so effectiveness as stimulators of protective immunity is decreased or lost.

Due to the lack of effective vaccines, enveloped viruses continue to pose a health risk to humans and nonhuman animals, and diseases caused by enveloped viruses have a huge economic impact. Improved vaccines are needed which are both safe and effective. For example, an improved method of inactivating enveloped viruses which preserves the immunogenicity of viral antigens, maintains virions intact, and poses little or no safety risk would be beneficial in alleviating diseases caused by enveloped viruses. The present application discloses such an improved method of viral inactivation, comprising delipidation of viral envelopes with MBCD.

Accordingly, the present invention provides for a method of preparing an inactivated enveloped virus comprising mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period. A concentration of MBCD in the first mixture is at least 5 mM to about 100 mM. Further, a concentration of MBCD in the first mixture is about 20 mM to about 40 mM. Further still, a concentration of MBCD in the first mixture is about 20 mM, about 30 mM, or about 40 mM.

The present invention provides for a method of preparing an inactivated enveloped virus comprising mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period; wherein a concentration of MBCD in the second mixture is at least 10 mM to about 100 mM. Further, a concentration of MBCD in the second mixture is about 30 mM to about 50 mM. Further still, a concentration of MBCD in the first mixture is about 30 mM, about 40 mM, or about 50 mM.

The present invention provides for a method of preparing an inactivated enveloped virus comprising mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period; wherein the first time period is about 15 minutes to about 24 hours. Further, the first time period is about 4 hours to about 24 hours. Further still, the first time period is about 4, 6, 8, 10, 12, 14, 16, 18, 20, 22, or 24 hours.

The present invention provides for a method of preparing an inactivated enveloped virus comprising mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period; wherein the second time period is about 4 hours to about 48 hours. Further, the second time period is about 24 hours to about 48 hours. Further still, the second time period is about 24, 30, 36, 40, 44, or 48 hours.

The present invention provides for a method of preparing an inactivated enveloped virus comprising mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period; wherein the temperature of the first mixture during the first time period is room temperature, or about 20° C. to about 25° C. Further, the temperature of the first mixture during the first time period is about 22° C. to about 24° C.

The present invention provides for a method of preparing an inactivated enveloped virus comprising mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period; wherein the temperature of the second mixture during the second time period is room temperature, or about 20° C. to about 25° C. Further, the temperature of the second mixture during the second time period is about 22° C. to about 24° C.

The present invention provides for a method of preparing an inactivated enveloped virus comprising mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period; wherein the enveloped virus is isolated from the first mixture prior to the step of obtaining the second mixture. Alternatively and without limitation, the second MBCD solution could be mixed directly with the first mixture. The direct mixing could be performed in the same inactivation vessel as the first mixing, or the first mixture could be moved to a new inactivation vessel prior to mixing with the second MBCD solution.

The present invention provides for a method of preparing an inactivated enveloped virus comprising mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period; wherein the first time period further comprises mixing of the first mixture. The stirring could be about 30 rpm to about 100 rpm. Preferably, the stirring could be about 40 rpm to about 60 rpm. Most preferably, the stirring could be about 50 rpm.

The present invention provides for a method of preparing an inactivated enveloped virus comprising mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period; wherein the second time period further comprises mixing of the second mixture. The stirring could be about 30 rpm to about 100 rpm. Preferably, the stirring could be about 50 rpm.

The present invention provides for a method of preparing an inactivated enveloped virus comprising mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period; wherein the enveloped virus is Porcine Reproductive and Respiratory Syndrome (PRRS) virus. The enveloped virus could also be Porcine Epidemic Diarrhea Virus (PEDV).

The present invention provides for a delipidated enveloped virus obtained by the method of mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period. Preferably, a concentration of MBCD in the first mixture is at least 5 mM to about 100 mM, or about 20 mM to about 40 mM. Preferably, a concentration of MBCD in the second mixture is at least 10 mM to about 100 mM, or about 30 mM to about 50 mM, or about 30 mM, about 40 mM, or about 50 mM. Preferably the first time period is about 15 minutes to about 24 hours, or about 4 hours to about 24 hours, or about 4, 6, 8, 10, 12, 14, 16, 18, 20, 22, or 24 hours. Preferably the second time period is about 4 hours to about 48 hours, or about 24 hours to about 48 hours, or about 24, 30, 36, 40, 44, or 48 hours. Preferably the temperature of the first mixture during the first time period is room temperature, or about 20° C. to about 25° C., or even about 22° C. to about 24° C. Preferably, the temperature of the second mixture during the second time period is room temperature, or about 20° C. to about 25° C., or even about 22° C. to about 24° C. Preferably, the enveloped virus is isolated from the first mixture prior to the step of obtaining the second mixture. Alternatively and without limitation, the second MBCD solution could be mixed directly with the first mixture. The direct mixing could be performed in the same inactivation vessel as the first mixing, or the first mixture could be moved to a new inactivation vessel prior to mixing with the second MBCD solution. Preferably, the first time period further comprises mixing of the first mixture, wherein the stirring could be about 30 rpm to about 100 rpm, about 40 rpm to about 60 rpm, or about 50 rpm. Preferably, the second time period further comprises mixing of the second mixture, wherein the stirring could be about 30 rpm to about 100 rpm, about 40 rpm to about 60 rpm, or about 50 rpm. Preferably, the enveloped virus is Porcine Reproductive and Respiratory Syndrome (PRRS) virus or Porcine Epidemic Diarrhea Virus (PEDV).

The present invention provides for a vaccine comprising a delipidated enveloped virus obtained by the method of mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period. Preferably, a concentration of MBCD in the first mixture is at least 5 mM to about 100 mM, or about 20 mM to about 40 mM. Preferably, a concentration of MBCD in the second mixture is at least 10 mM to about 100 mM, or about 30 mM to about 50 mM, or about 30 mM, about 40 mM, or about 50 mM. Preferably the first time period is about 15 minutes to about 24 hours, or about 4 hours to about 24 hours, or about 4, 6, 8, 10, 12, 14, 16, 18, 20, 22, or 24 hours. Preferably the second time period is about 4 hours to about 48 hours, or about 24 hours to about 48 hours, or about 24, 30, 36, 40, 44, or 48 hours. Preferably the temperature of the first mixture during the first time period is room temperature, or about 20° C. to about 25° C., or even about 22° C. to about 24° C. Preferably, the temperature of the second mixture during the second time period is room temperature, or about 20° C. to about 25° C., or even about 22° C. to about 24° C. Preferably, the enveloped virus is isolated from the first mixture prior to the step of obtaining the second mixture. Alternatively and without limitation, the second MBCD solution could be mixed directly with the first mixture. The direct mixing could be performed in the same inactivation vessel as the first mixing, or the first mixture could be moved to a new inactivation vessel prior to mixing with the second MBCD solution. Preferably, the first time period further comprises mixing of the first mixture, wherein the stirring could be about 30 rpm to about 100 rpm, about 40 rpm to about 60 rpm, or about 50 rpm. Preferably, the second time period further comprises mixing of the second mixture, wherein the stirring could be about 30 rpm to about 100 rpm, or about 50 rpm. Preferably, the enveloped virus is Porcine Reproductive and Respiratory Syndrome (PRRS) virus or Porcine Epidemic Diarrhea Virus (PEDV).

The present invention provides for a vaccine comprising a delipidated enveloped virus obtained by the method of mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period; wherein the vaccine further comprises at least one of an adjuvant, a stabilizer, a preservative, and a blending diluent. Preferably, the adjuvant is an aqueous polymeric adjuvant, wherein the polymer is acrylate or polyacrylate. Preferably, the stabilizer comprises at least one of sugars, carbohydrates, proteins, and gelatins. Preferably, the preservative is an antibiotic or biostatic compound that retards, inhibits, or prevents the growth, metabolic activity, or multiplication of microorganisms. Preferably, the blending diluent is water, a phosphate buffered saline, a cell culture medium, or other solution comprising physiological salinity and pH.

The present invention provides for use of a delipidated enveloped virus obtained by the method of mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period; wherein the use comprises treatment of a disease or symptom caused by an enveloped virus.

The present invention provides for use of a delipidated enveloped virus in the manufacture of a medicament for the treatment of a disease or symptom caused by an enveloped virus; wherein the delipidated enveloped virus is obtained by the method of mixing a solution comprising an enveloped virus with a first MBCD solution to obtain a first mixture; incubating the first mixture for a first time period; mixing the enveloped virus from the first mixture with a second MBCD solution to obtain a second mixture; and incubating said second mixture for a second time period.

As used herein, an "enveloped virus" is any virus having a lipid bilayer membrane, or envelope, surrounding a nucleoprotein core. Viral envelopes are typically derived from host cell membranes and contain phospholipids, glycolipids, sphingolipids, and sterols such as cholesterol. Enveloped viruses include viruses which have genomes encoded by either DNA or RNA. Species of enveloped viruses include, without limitation: herpesviruses, poxviruses, iridoviruses, hepadnaviruses, retroviruses, orthomyxoviruses, arenaviruses, bunyaviruses, paramyxoviruses, mononegaviruses, rhabdoviruses, filoviruses, coronaviruses, arteriviruses, flaviviruses, and togaviruses. New enveloped viruses are being discovered, and enveloped viruses are being classified and reclassified as each virus is better characterized. A more complete description of enveloped viruses could be found in texts such as Fields Virology (D. M. Knipe and P. M. Howley, eds., Lippincott Williams & Wilkins, Philadelphia, Pa., USA, 2013), now in its sixth edition.

The term "virus" as used herein could mean either the species of virus or, interchangeably, an individual infectious unit or units containing nucleic acids, proteins, and an envelope. A "viral particle" is an individual infectious unit, and this term is synonymous with the term "virion."

"Delipidation" is the process of removing or depleting lipids from the viral envelope. Delipidation is measured by the amount of cholesterol removed from viral particles by MBCD. However, MBCD could also extract, remove or deplete other lipids, such as phospholipids. MBCD has also been shown to interact with some proteins, although the process described herein minimizes loss of proteins from viral proteins as a result of MBCD-mediated delipidation.

"Infectivity" is the ability of a virus to establish an infection within a host cell, which is any cell from a human or non-human animal capable of supporting the replication of the virus. Infectivity can be measured, for example, by the number or percentage of host cells infected by a set number of viral particles, or by the number or percentage of viral particles necessary to infect a host cell. Viral particles can be enumerated operationally, such as by the determination of the number of plaque-forming units (PFU) within a volume of viral particles. Viral particles can also be measured physically, such as by the presence of a particular viral protein detected, for example, by an enzyme-linked immunosorbent assay (ELISA), or by the measurement of the number of copies of a viral genome present in a solution, detected, for example, by real-time quantitative polymerase chain reaction (qPCR).

An "antigen" is any molecule capable of being specifically detected by the immune system of an organism. Typically a viral antigen is a viral protein encoded by the viral genome. The presence of viral antigens can be specifically detected by both T lymphocytes and B lymphocytes. "Immunogenicity" refers to the ability of an antigen to elicit an immune response. For vaccines, the immunogenicity of a viral antigen would preferentially result in protective immunity in an animal which would reduce, mitigate, or ameliorate a viral infection.

In contrast to an antigen, an "adjuvant" is a non-specific stimulator of an immune response. An adjuvant could stimulate the innate immune response by binding and activating a pattern recognition receptor (PRR). Such stimulators of PRRs could be, for example, viral or bacterial nucleic acids, lipids from bacteria or parasites, or bacterial proteins or toxins, or any artificially-constructed mimic of such molecules. Adjuvants also include, without limitation: inorganic compounds that aggregate antigens to facilitate recognition by B lymphocytes or uptake by phagocytes, such as alum, aluminum hydroxide, aluminum phosphate, calcium phosphate hydroxide or ammonium sulfate; oils; and detergents. Adjuvants could also be host mediators of immune signaling, such as, without limitation, cytokines, lymphokines, chemokines, interferons, anaphylatoxins, growth factors, differentiation factors, and adhesion molecules.

As used herein, the terms "treating", "to treat", or "treatment", include restraining, slowing, stopping, reducing, ameliorating, or reversing the progression or severity of an existing symptom, disorder, condition, or disease. A treatment may be applied prophylactically or therapeutically.

As used herein, "administering to an animal" includes cutaneous, subcutaneous, intramuscular, mucosal, submucosal, transdermal, oral or intranasal administration. Administration could include injection or topical administration.

The following experimental examples are illustrative of the delipidation processes. It will be appreciated that other embodiments and uses will be apparent to those skilled in the art and that the invention is not limited to these specific illustrative examples or preferred embodiments. Enveloped viruses contain different levels of cholesterol in their envelopes, depending on, for example without limitation, the type and species of the enveloped virus and the host cell in which the enveloped virus replicates. As one skilled in the art will appreciate, the delipidation processes described herein may require optimization for each particular virus stock. The membranes of microorganisms may contain cholesterol, hopanoids, or other sterols and sterol-like molecules, and thus pathogens other than viruses may also be inactivated by the methods disclosed herein.

EXAMPLE 1

The human influenza virus H1N1 A/WSN/33 strain is delipidated using the procedures below. In the examples below, delipidation of the influenza virus (IFV) impairs infectivity. Because the delipidation method of the present invention preserves viral envelope proteins, animals inoculated with the delipidated IFV are expected to develop immunogenic responses that protect them from infection of a pathogenic dose of the virulent virus.

Reagents:

The human influenza virus H1N1 A/WSN/33 strain and its host cell line MDCK are available from Wuxi AppTec (Shanghai, China). Other reagents include MEM (Invitrogen, Carlsbad, Calif.); EMEM (Sigma-Aldrich, St. Louis, Mo.); ULTRAMDCK™ Serum-Free Medium (Lonza, Inc., Allendale, N.J.); fetal bovine serum (FBS; Invitrogen); 0.25% Trypsin-EDTA (ethylenediaminetetraacetic acid; Invitrogen); methyl-β-cyclodextrin (MBCD, Sigma-Aldrich); AMPLEX Red Cholesterol Assay Kit (Invitrogen); PIERCE™ BCA Protein Assay Kit (Rockford, Ill.); and MTT (Sigma-Aldrich).

Propagation of H1N1 A/WSN/33 Influenza Virus in MDCK Cell Line:

Cells are seeded with IFV according to the following procedure. Medium is removed from MDCK cells grown in T-75 flasks, the MDCK cell monolayers are rinsed with 5 mL of PBS at room temperature, and the cells are detached with 1.5 mL of trypsin/EDTA at 37° C. Cells are resuspended in 10 mL MEM containing 10% FBS and pelleted by centrifugation at 800 rpm for 5 minutes at 4° C. Cells are resuspended in MEM containing 10% FBS, and the cell density is adjusted to $2.5 \times 10^5$ cell/mL. Fifteen mL of the MDCK cell suspension are seeded into each T-75 flask, and flasks are placed at 37° C. with 5% $CO_2$ and incubated overnight.

When the MDCK cells are more than 90% confluent, MEM is removed from the T75 flasks, 5 mL EMEM maintenance media containing 1% FBS and 1 µg/mL trypsin is added, and the cells are infected with influenza virus at a Multiplicity of Infection (MOI) of 0.01. Flasks are incubated for 60-90 minutes at 37° C. with 5% $CO_2$ and gently shaken every 15 minutes. Ten mL EMEM maintenance media containing 1% FBS and 1 µg/mL trypsin are added to each flask, and the flasks are incubated for 48 hours at 37° C. and 5% $CO_2$. When approximately 80% of the cytopathic effect (CPE) of the virus is achieved (generally after about 48 hours), the culture supernatants are harvested to obtain IFV.

Purification and Titration of H1N1 A/WSN/33 IFV:

IFV is purified according to the following procedure. The collected culture supernatant is centrifuged at 3,000 rpm for 20 minutes to remove cell debris, and the supernatant is collected. The supernatant is centrifuged at 38,000 rpm for 60 minutes to pellet the IFV. The IFV pellets are resuspended in an appropriate volume of physiologically buffered saline (PBS) to give a final titer of $>1.0 \times 10^9$ plaque-forming units/mL (PFU/mL). Aliquots of 100 µL of this concentrated IFV stock solution are stored at −80° C.

The IFV are titrated for in vitro infectivity using the following procedure. Using the cell culture and transfer procedures above, MDCK cells are suspended in MEM containing 10% FBS at a final density of $2.5 \times 10^5$ cell/mL. Two mL of the MDCK cell suspension are added to each well of a 6-well plate, and the plates are incubated overnight at 37° C. with 5% $CO_2$. Viral stocks are thawed in a 37° C. water bath, followed by centrifugation at 500×g for 10 minutes at 4 C. A 1/10 dilution series of the stock solution is prepared and stored at 4° C. until use, using ULTRAMDCK™ Serum Free Medium and 2.5 µg/mL trypsin as the dilution buffer.

When the cells are at least 90% confluent, the medium is removed, and 0.5 mL dilution buffer and 0.5 mL of the virus dilution are added into each well. For the negative control, 1.0 mL dilution buffer is used. The plates are gently shaken immediately after each dilution is added. Plates are incubated for 60-90 minutes at 37° C. in 5% $CO_2$ and rocked every 15 minutes. Each well of each 6-well plate is then overlaid with 3 mL of a 1:4 mixture of 2.5% low melting point agarose in PBS solution and dilution buffer at 37° C. The plates are incubated at room temperature for 15 minutes to allow the overlay mixture to solidify; then the plates are incubated at 37° C. with 5% $CO_2$ for 3 days.

Plaques are visualized using the following procedure. After the plaques are fully developed (3 days post-infection), 1 mL 4% paraformaldehyde is added, and the plates are incubated at room temperature for 1 hour. Solubilized agarose is discarded, and 0.1 mL of 0.5% crystal violet is added to each well. The number of plaques is counted after 15 minutes of incubation and converted to a titer based on the dilution factors.

Delipidation:

The delipidation process for the purified IFV is run in two parallel reactions: a solvent treatment comprising contacting the IFV with MBCD and a mock treatment, where the IFV are treated in the same manner, but without exposure to MBCD. The same titer of IFV is used in both the mock and solvent treatments. The IFV in the mock treatment can be titered to provide an indirect measure of the amount of delipidated IFV remaining after the solvent treatment.

Solvent and mock treatments are conducted according to the following procedure. Aliquots (100 µL) of the IFV stock prepared above ($>1.0 \times 10^9$ PFU/mL) are diluted into 900 µL PBS in Eppendorf tubes to achieve a final titer of 1.0-5.0×

$10^8$ PFU/mL. MBCD in PBS is added to a final concentration of 50 mM for the solvent treatment, or an equal volume of PBS is added to the mock treatment. Eppendorf tubes are then capped and sealed with parafilm. All the samples are secured in an SHZ-82 constant-temperature orbital air-bath shaker (Changzhou Guohua Appliance Co., China) preheated to 37° C. The solvent- and mock-treated samples are spun at an orbital rotation speed of 220 rpm at 37° C. for either 30 minutes or 45 minutes. The samples are spun in a micro-centrifuge for 1 minute, and the supernatants containing IFV are transferred to ultracentrifuge tubes. Tubes are centrifuged at 200,000×g (OPTIMA™ L-100XP; Beckman Coulter, Inc., Indianapolis Ind.) for 30 minutes to pellet the IFV, and the supernatants are discarded. The IFV pellets are resuspended in 1/10 of original volume added to each Eppendorf tube above and stored at −80° C. until further analyses.

Characterization of Delipidated IFV:

The protein content of the delipidated and mock-treated IFV is determined using a BCA assay (PIERCE™ BCA Protein Assay Kit) according to the manufacturer's instructions. The cholesterol content is determined using a cholesterol assay (AMPLEX® Red Cholesterol Assay Kit, Life Technologies, Grand Island, N.Y.) performed according to manufacturer's instruction. In vitro infectivity is measured using the same titration procedures as set forth above.

Hemagglutination (HA) activity is determined as follows. Freshly isolated chicken blood is washed three times with PBS, and the red blood cells (RBC) are resuspended in PBS at a concentration of 1%. Virus dilutions (50 µL) are made in PBS and mixed with 50 µL of the RBC suspension. The mixture is added to individual wells in a 96-well plate and the RBC are allowed to settle for 45 minutes. The wells are judged to be HA negative (i.e. no agglutination of RBC) if a dot or pellet of RBC is present, and a well is judged to be positive if a smooth suspension of RBC is present.

Two batches of delipidated and mock-treated IFV samples are prepared according the procedure described above. The IFV stock used for the tests has a titer of $2.2 \times 10^{10}$ PFU/mL. In the first batch ("preparation A"), the delipidation time is 30 minutes; in the second batch ("preparation B"), the delipidation time is 45 minutes. After ultracentrifugation, the delipidated and the mock-treated samples are characterized.

In vitro infectivity shows that the PFU of the delipidated samples are about ~1/7,000 of those of the corresponding mock samples. The infectivity results are shown in TABLE 1, below. Despite the difference in titers, the protein contents of the various samples are within 10% of each other. The protein content of the delipidated IFV from preparation A is 97% of the mock sample; and the protein content of the delipidated IFV from preparation B is 93% of the mock sample (see TABLE 1). It is also observed that after the treatment approximately 20% of starting material is recovered, as determined by the protein content. The percentage recovery based on protein content is comparable with the measured titers of the starting material ($2.2 \times 10^9$ PFU/mL) and the mock-treated samples ($4.0 \times 10^8$ PFU/mL, which is 18% of the starting titer). After the delipidation, less than 2% of cholesterol remains, compared to the mock treatment (see TABLE 1).

TABLE 1

| Treatment | | In vitro infectivity (PFU/mL) | Protein content (mg/mL) | Cholesterol content (µg/mL) |
|---|---|---|---|---|
| Preparation A (30 minutes) | Mock | $4 \times 10^8$ | 1.49 | 16.4 |
| | Delipidated | $6 \times 10^4$ (1/6667) [a] | 1.44 (97%) [b] | 0.25 (1.5%) [b] |

TABLE 1-continued

| Treatment | | In vitro infectivity (PFU/mL) | Protein content (mg/mL) | Cholesterol content (µg/mL) |
|---|---|---|---|---|
| Preparation B (45 minutes) | Mock | $2 \times 10^8$ | 1.39 | 15.9 |
| | Delipidated | $3 \times 10^4$ (1/6667) [a] | 1.29 (93%) [b] | 0.1 (0.6%) [b] |

Notes:
[a] fraction of infectivity, compared to the mock treatment;
[b] percentage compared to the mock treatment.

The mock treatment indicates that physical treatment (shaking and centrifugation) results in a loss of titer and protein. Delipidation by MBCD preferentially removes cholesterol, but not protein, from IFV. Further, IFV treated with MBCD has less in vitro infectivity, but infectivity was not completely abolished.

Comparison of IFV Delipidation with Diisopropyl Ether and MBCD:

In addition to MBCD, another lipid solvent, diisopropyl ether (DIPE) is used to delipidate IFV. IFV samples of the same starting material are treated with different concentrations of DIPE or with 50 mM MBCD. Aliquots of the same quantity of IFV are treated with 2%, 4%, 8%, or 12% DIPE or 50 mM MBCD for 37° C. for 30 minutes. After a brief centrifugation at 2,000×g for 3 minutes, visible solvent is removed, and the aqueous materials are left to dry in a fume hood for 20 minutes. The samples are then centrifuged at 200,000×g for 30 minutes to recover virus particles. The in vitro infectivity, HA activities, protein content, and cholesterol content of the IFV are shown in TABLE 2.

DIPE treatment at concentration up to 12% is not as effective in removing cholesterol as 50 mM MBCD under the same conditions. While 12% DIPE removes about 80% of cholesterol from IFV, 50 mM MBCD removes more than 98%. The IFV infectivities of these two treatments are reduced 32- and 2250-fold, respectively, compared to the mock-treatment, as determined by comparing the PFU/mL. The removal of cholesterol by both solvents is relatively specific, because protein content is reduced by less than 20% in the various treatments. Within the ability to quantify haemagglutination (HA) activity, 50 mM MBCD affects HA activity by the same degree as 2%-8% DIPE.

TABLE 2

| Treatment | PFU/mL | HA units | Protein (mg/mL) | Cholesterol (µg/mL) |
|---|---|---|---|---|
| Mock | $9.0 \times 10^8$ | 64 | 0.39 | 8.26 |
| 2% DIPE | $1.2 \times 10^8$ | 32 | 0.39 (100%) [a] | 6.61 (80.0%) [a] |
| 4% DIPE | $1.4 \times 10^8$ | 32 | 0.32 (82%) [a] | 4.88 (59.1%) [a] |
| 8% DIPE | $9.0 \times 10^7$ | 32 | 0.36 (92%) [a] | 3.47 (42.0%) [a] |
| 12% DIPE | $2.8 \times 10^7$ | 16 | 0.33 (85%) [a] | 1.81 (21.9%) [a] |
| 50 mM MBCD | $4.0 \times 10^5$ | 32 | 0.33 (85%) [a] | 0.14 (1.7%) [a] |

Note:
[a] percentage compared to the mock treatment.

Treatment with Solvents for 45 Minutes:

The treatments above are repeated, except that the MBCD treatment duration is extended from 30 to 45 minutes. The results are shown below in TABLE 3.

TABLE 3

| Treatment | PFU/mL | HA units | Protein (mg/mL) | Cholesterol (µg/mL) |
|---|---|---|---|---|
| Mock [a] | $1.2 \times 10^7$ | 32 | 0.42 | 6.16 |
| 10% DIPE [a] | $1.0 \times 10^5$ | 16 | 0.21 (50%) [c] | 1.32 (21.4%) [c] |

TABLE 3-continued

| Treatment | PFU/mL | HA units | Protein (mg/mL) | Cholesterol (μg/mL) |
|---|---|---|---|---|
| 50 mM MBCD[b] | $1.0 \times 10^3$ | 32 | 0.39 (94%) [c] | 0.15 (2.5%) [c] |

Note:
[a] end-over-end rotation at 37° C. for 30 minutes.
[b] end-over-end rotation at 37° C. for 45 minutes.
[c] percentage compared to the mock treatment.

As with a 30 minute treatment, a 45 minute treatment with 50 mM MBCD removes about 97% of cholesterol for IFV and renders the virus over 10,000-fold less infectious in vitro, compared to the mock treatment. In contrast, 10% DIPE (30 minute treatment) is less effective in removing cholesterol (about 80%) and results in about a 120-fold decrease in infectivity in vitro. The HA activity is not measurably affected by MBCD, while it was measurably reduced by 10% DIPE. The protein content is reduced to 50% after 10% DIPE treatment, compared to a 6% reduction by 50 mM MBCD.

The two sets of experiments presented herein demonstrate that 50 mM MBCD selectively removes cholesterol and renders the delipidated IFV less infectious while maintaining most of the proteins. However, neither of these treatments was able to completely abolish infectivity and thus completely inactivate the virus, so further optimization of the procedure is required to completely inactivate influenza viruses. The further optimization could include, without limitation, increasing time of MBCD treatment and treating the virus a second time period with MBCD.

EXAMPLE 2

Treatment of PRRSV with MBCD selectively removes cholesterol, decreases viral infectivity, and maintains most of the viral protein content.

Reagents:

The PRRSV virus strain used in this example is RESP (Jiangsu Academy of Agriculture Sciences, China). The host cell used is Marc-145 (Wuxi AppTec, Shanghai, China). Other reagents used are the same as in Example 1, above, except for DMEM (Invitrogen), which is used when culturing Marc-145 cells.

Propagation of PRRSV in Marc-145 Cells:

Cells are seeded with PRRSV according to the following procedure. Medium is removed from Marc-145 cells grown in T-75 flasks, the Marc-145 cell monolayers are rinsed with 5 mL of PBS at room temperature, and the cells are detached with 1.5 mL of trypsin/EDTA at 37° C. Cells are resuspended in 10 mL DMEM medium containing 10% FBS and pelleted by centrifugation at 800 rpm for 5 minutes at 4° C. Cells are resuspended in DMEM medium containing 10% FBS, and the cell density is adjusted to $2.5 \times 10^5$ cell/mL. Fifteen mL of the Marc-145 cell suspension are seeded into each T75 flask, and flasks are placed at 37° C. with 5% $CO_2$ and incubated overnight.

When the Marc-145 cells are more than 90% confluent, DMEM is removed from the T-75 flasks, 5 mL EMEM maintenance media containing 2% FBS is added, and the cells are infected with PRRSV at a MOI of 0.1. Flasks are incubated for 60-90 minutes at 37° C. with 5% $CO_2$ and gently shaken every 15 minutes. Ten mL EMEM maintenance media containing 2% FBS are added to each flask, and the flasks are incubated for 96 hours at 37° C. and 5% $CO_2$. When 80% of CPE is achieved (generally 96 hours), the culture supernatants are harvested to obtain PRRSV.

Purification of PRRSV:

PRRSV is purified according to the following procedure. The collected culture supernatant is centrifuged at 3,000 rpm for 20 minutes to remove cell debris, and the supernatant is collected. The supernatant is centrifuged at 100,000×g for 60 minutes to pellet the PRRSV. The PRRSV pellets are resuspended in an appropriate volume of physiologically buffered saline (PBS) to a titer of about $1 \times 10^9$ PFU/mL. Aliquots of 100 μL concentrated PRRSV are stored at −80° C.

The PRRSV are titrated for in vitro infectivity using the following procedure. Using the cell culture and transfer procedures above, Marc-145 cells are suspended in DMEM containing 10% FBS at a final density of $1.5 \times 10^5$ cell/mL. Two mL of the Marc-145 cell suspension are added to each well of a 6-well plate, and the plates are incubated overnight at 37° C. with 5% $CO_2$. Virus samples are thawed in a 37° C. water bath, followed by centrifugation at 500×g for 10 minutes at 4° C. A 1/10 dilution series of viruses is prepared and stored at 4° C. until use, using EMEM as the dilution buffer.

When the Marc-145 cells are at least 90% confluent, the medium is removed, and 0.5 mL dilution buffer and 0.5 mL of the virus dilution are added into each well. For the negative control, 1.0 mL dilution buffer is used. The plates are gently shaken immediately after each dilution is added. Plates are incubated for 60-90 minutes at 37° C. in 5% $CO_2$ and rocked every 15 minutes. Each well of each 6-well plate is then overlaid with 3 mL of a 1:4 mixture of 2.5% low melting point agarose in PBS solution and dilution buffer at 37° C. The plates are incubated at room temperature for 15 minutes to allow the overlay mixture to solidify, and then the plates are incubated at 37° C. with 5% $CO_2$ for 96 hours.

Plaques are visualized using the following procedure. After the plaques are fully developed (96 hours post-infection), 1 mL 4% paraformaldehyde is added, and the plates are incubated at room temperature for 1 hour. Solubilized agarose is discarded, and 0.5 mL of 0.5% crystal violet is added to each well. The number of plaques is counted after 15 minutes of incubation with the crystal violet and converted to a titer based on the dilution factors.

In Vitro Propagation of PRRSV:

A PRRSV titer greater than $1 \times 10^7$ PFU/mL is preferred for the protein and cholesterol assay. The propagation of PRRSV-RESP strain in Marc-145 cells yields a concentrated virus sample having a titer $>1 \times 10^8$ PFU/mL.

Delipidation of PRRSV:

Solvent and mock treatments are conducted according to the following procedure. One hundred μL aliquots of the concentrated PRRSV stock at about $1 \times 10^9$ PFU/mL are diluted into 900 μL PBS in Eppendorf tubes to achieve a final titer of $1.0-5.0 \times 10^8$ PFU/mL. MBCD in PBS is added to the desired concentration for the solvent treatment, or an equal volume of PBS is added for the mock treatment. Eppendorf tubes are then capped and sealed with parafilm. All the samples are secured in an SHZ-82 constant-temperature orbital air-bath shaker (Changzhou Guohua Appliance Co., China) preheated to 37° C. The solvent- and mock-treated samples are spun at an orbital rotation speed of 220 rpm at 37° C. for the desired time. The respective samples are spun in a micro-centrifuge for 1 minute, and the supernatants containing IFV are transferred to ultracentrifuge tubes. Tubes are centrifuged at 100,000×g (OPTIMA™ L-100XP centrifuge; Beckman Coulter, Inc., Indianapolis Ind.) for 30 minutes to pellet the PRRSV, and the supernatants are discarded. The PRRSV pellets are resuspended in 200 µL PBS and stored at −80° C. until further analyses.

Characterization of Delipidated PRRSV:

The protein content of the delipidated and mock-treated PRRSV is determined using a BCA assay (PIERCE™ BCA Protein Assay Kit) according to the manufacturer's instructions. The cholesterol content also is determined using a cholesterol assay (Amplex® Red Cholesterol Assay Kit, Life Technologies, Grand Island, N.Y.) performed according to manufacturer's instruction. In vitro infectivity is measured using the same procedures as set forth above.

Concentration Dependence of MBCD:

In the first delipidation experiment, PRRSV is delipidated with 5, 10, 20, 30, and 50 mM MBCD for 60 minutes at 37° C. After ultracentrifugation, the mock-treated and delipidated samples are tested for in vitro infectivity in the Marc-145 cells, and protein and cholesterol contents are determined, using the procedures set forth above. The infectivity, protein content, and cholesterol content of the delipidated PRRSV are shown in TABLE 4.

TABLE 4

| Treatment | In Vitro Infectivity (PFU/mL) | Protein Content (mg/mL) | Cholesterol Content (µg/mL) |
| --- | --- | --- | --- |
| Mock | $1.6 \times 10^7$ | 4.46 | 11.64 |
| 5 mM MBCD | $1.4 \times 10^7$ | 3.94 (88%) [a] | 9.82 (84%) [a] |
| 10 mM MBCD | $7.0 \times 10^6$ | 4.00 (89%) [a] | 4.66 (40%) [a] |
| 20 mM MBCD | $2.8 \times 10^6$ | 4.05 (90%) [a] | 4.46 (38%) [a] |
| 30 mM MBCD | $1.2 \times 10^5$ | 4.36 (97%) [a] | 4.00 (34%) [a] |
| 50 mM MBCD | $4.2 \times 10^4$ | 4.40 (98%) [a] | 3.29 (28%) [a] |

Note:
[a] percentage compared to the mock treatment.

The titer of the starting PRRSV-RESP stock is $1.0 \times 10^8$ PFU/mL, of which 0.1 mL is mixed with 0.9 mL PBS, together with appropriate amount of MBCD. After orbital shaking at 220 RPM for 60 min at 37° C., the virus samples are pelleted by ultracentrifugation and suspended in a final volume of 0.2 mL of PBS. The titer of the mock-treated sample is $1.6 \times 10^7$ PFU/mL (TABLE 4), suggesting that more than 30% of viral activity is recovered after the mock treatment. MBCD treatment reduces the infectivity and cholesterol content in a largely concentration-dependent manner, while the 88%-98% of the total protein content is recovered at all MBCD concentrations (see TABLE 4). After treatment with 50 mM MBCD, the delipidated PRRSV retains about 28% of starting amount of cholesterol compared to the mock sample, and the PRRSV infectivity is reduced by about 380-fold, but again is not completely abolished.

Blind Passage Assay of a Dellpidated PRRSV Sample:

The titer of one of the delipidated PRRSV samples (100 mM MBCD for 90 minutes) is under the limit of detection. This raises the question whether there are any infectious virus particles in the sample. To address the question of whether such infectious virus particles are present, a new sample is delipidated with 100 mM MBCD for 90 minutes and is subjected to the blind passage assay described below. While a control PRRSV-RESP sample has a titer of $1.6 \times 10^6$ PFU/mL, no plaques are detected by the blind passage assay from the PRRSV sample delipidated with 100 mM MBCD for 90 minutes. Delipidation with 100 mM MBCD for 90 minutes likely inactivates PRRSV-RESP completely.

The blind passage assay is conducted according to the following procedure. One hundred µL of the delipidated PRRSV sample is transferred to each well of a 6-well plate containing the Marc-145 cells, prepared by the procedure above. The plates are incubated for 4 days at 37° C. in 5% $CO_2$. Three consecutive freeze-thaw cycles are preformed to lyse the cells, and the supernatants containing PRRSV are harvested and centrifuged at 800 rpm for 5 min at 4° C. Four hundred µL of the supernatant are transferred to a flask of Marc-145 cells. The flasks are incubated for 4 days at 37° C. and 5% $CO_2$. The freeze-thaw cycles are repeated, and the supernatants are again harvested, centrifuged, and transferred to a flask of Marc-145 cells as before. The freeze-thaw cycles are repeated once more, the supernatants are again harvested and centrifuged, and the supernatants containing the PRRSV are frozen at −80° C. until further use. The PRRSV titer of the final, harvested samples is determined using Marc-145 cells as above.

EXAMPLE 3

The objective of this study was to determine the time dependency for the inactivation of PRRSV strain ND 99-14 through a delipidation method that utilizes methyl β cyclodextrin (MBCD). MBCD was purchased in powder form from CTD, Inc. (Alachua, Fla.). A 300 mM stock solution was prepared by adding 1000 mL of water to 280 g of MBCD to generate the stock solution.

Virus Delipidation:

Inactivation kinetics experiments were conducted using PRRSV strain ND99-14, described in application U.S. Ser. No. 62/296,658, filed Feb. 18, 2016. In general the method involves the addition of MBCD at a final concentration of 40 mM and a total of 72 hours of incubation time at room temperature with constant mixing. Addition of MBCD occurs in 2 steps, 20 mM to start the inactivation process, an additional 20 mM of MBCD is added 24 hour later and incubated an additional 48 hours at room temperature with constant mixing. Room temperature is between about 20° C. and about 25° C., and optimally between about 22° C. and about 24° C.

A 300 mM stock of MBCD solution was initially added to the virus to a final concentration of 20 mM by adding 567 mL of MBCD solution to 8.5 L of virus stock. The virus was incubated for 24 hours at room temperature with mixing at 50 rpm. 30 mL of virus was collected at 0 hours, 15 minutes, 4, 8, 12, 16, 20 and 24 hours post MBCD addition. Aliquots for each time point were stored at 4° C. and −70° C. until further use.

After the 24 hour sample was collected, virus was transferred to a new container. An additional 20 mM of MBCD was added (650 mL MBCD added to 9.75 L of virus stock) to arrive at a final concentration of 40 mM. The virus was incubated an additional 48 hours at room temperature. 30 mL of virus was collected at 30, 36, 42, 48, 60, 72, 84 and 96 hours following the first MBCD addition. Aliquots for each time point were stored at 4° C. and −70° C. until further use.

Virus Measurement:

Ten-fold serial dilutions ($10^{-1}$-$10^{-9}$) of mock inactivated and inactivated virus were added to MARC145 cells cultured on 96 well plates. The plates were incubated at 37° C. and 5% $CO_2$ for 96 hours to allow live virus to infect cells. Virus replication was determined by observation of cytopathic effect (CPE) due to virus infection of the MARC145 cells. Each well containing a virus dilution was scored either positive or negative with regards to CPE and the resulting numbers of positive or negatice wells for each dilution were used to determine the $TCID_{50}$/mL using the Reed-Muench $TCID_{50}$ calculation. The mock inactivated virus was treated to the same media and temperature conditions as the inactivated virus without the addition of the inactivation agent.

Three consecutive blind passages of mock inactivated and inactivated virus as well as a media only control were performed using MARC145 cells cultured on T-225 flasks. The inactivated and control samples were added to a 2 day culture of MARC145 cells and incubated for 7 days at 37° C. and 5% $CO_2$ (3 mL of sample into 27 mL of media). The flasks were visually inspected for the presence of CPE. Each flask was scored either positive (+) or negative (−) with regards to CPE and recorded. The supernatants from the flasks were harvested and added to a new set of T-225 flasks containing 2 day cultures of MARC-145 cells and incubated for 7 days at 37° C. and 5% $CO_2$. The above process was repeated twice to obtain CPE observations for 3 consecutive virus passages.

PRRS virus titers were determined for all time points collected during the 96 hour incubation period using samples stored at 2 different temperatures as shown. 0 indicates the titer was undetectable or undetermined by the PRRS Live Virus$TCID_{50}$ determination assay. The results presented in Table 5 demonstrated that 40 mM added in a 2 step process was able to inactivate PRRS virus with a titer of at least 8 $log_{10}$ $TCID_{50}$/mL. Higher titers demonstrated incomplete inactivation with 20 mM MBCD, but virus was undetectable after the second addition of MBCD to bring up the concentration to 40 mM. The results also showed that time was less of a contributing factor for inactivation. Longer incubation times at a given concentration of MBCD did not increase the level of inactivation. A 20 mM concentration of MBCD reduced live virus by approximately 2.5 logs after 15 minutes of incubation and the level of live virus detected remained constant for 24 hours. A second addition of 20 mM MBCD at 24 hours of incubation inactivated the virus to undetectable levels by the next time point sample collected (30 hours). Differences in viability were also observed in the presence of 40 mM MBCD at different storage temperatures. Time point samples with detectable live virus had at least 100 fold less virus when stored at −70° C. versus 4° C.

TABLE 5

| Hour | Samples stored at 4° C. | Samples stored at −70° C. |
|---|---|---|
| 0.25 | 5.8[a] | 3.3 |
| 4 | 5.8 | nd |
| 8 | 5.9 | 2.8 |
| 12 | 5.6 | 3.2 |
| 16 | 5.6 | 3.2 |
| 20 | 5.6 | 3.4 |
| 24 | 5.6 | 3.6 |
| 30 | 0 | 0 |
| 36 | 0 | 0 |
| 42 | 0 | 0 |
| 48 | 0 | 0 |
| 56 | 0 | 0 |
| 64 | 0 | 0 |
| 72 | 0 | 0 |
| 84 | 0 | 0 |
| 96 | 0 | 0 |

[a]$Log_{10}$ $TCID_{50}$/mL

EXAMPLE 4

The objective of this study was to evaluate the safety and efficacy of experimental inactivated PRRSV vaccines in a vaccination-challenge study. Vaccines were evaluated on their ability to reduce lung lesions and viremia levels. Vaccine characteristics of interest included storage temperature, number of doses (1 vs 2) and adjuvant addition. The study was conducted in BSL-2 facilities at Veterinary Resources, Inc., Cambridge, Iowa. Laboratory assays were conducted at the Iowa State University Veterinary Diagnostic Laboratory, Ames, Iowa and South Dakota State University Veterinary Diagnostic Laboratory, Brookings, S. Dak. Sixty (60) clinically healthy, weaned pigs about 3 weeks of age that were seronegative to PRRSV were enrolled in the study. Pigs were ranked by decreasing body weight and 10 blocks of 6 animals each were formed. Pigs were randomly assigned to one of six treatment groups (10 pigs per group). Treatment groups included a non-vaccinated control group (T01) and five groups vaccinated with experimental inactivated PRRSV vaccines. The vaccines were inactivated by means of delipidation using methyl-beta-cyclodextrin (MBCD). Groups T02 and T03 vaccines contained no adjuvant and were stored at either 2-8° C. (T02) or −20° C. (T03). Groups T04 and T05 vaccines contained MONTANIDE™ Gel 01 adjuvant (Seppic) and were administered either once (T04) or twice (705). Group T06 vaccine contained MONTANIDE™ IMS 1313 VG N PR adjuvant (Seppic) and was given twice.

Pigs were fed standard commercial medicated (CTC/DENAGARD®) starter diets (NRC, 2012) ad libitum via top-load feeders. Pigs had access to clean drinking water ad libitum via nipple waterers. All study pigs were treated with EXCEDE® 10 days post-vaccination (DPV). In addition, all pigs were treated with a single dose of VITAL E®-500 and another treatment of EXCEDE® 21 DPV. All medications were administered according to label directions.

Vaccines

PRRSV strain SD 11-21 (passage level 84) was used as the antigen in the current study. SD11-21 is a field strain that was adapted for growth in cell culture through 84 passages through the MARC-145 cell line as well as three rounds of plaque purification and sucrose gradient centrifugation, as described in application U.S. Ser. No. 62/296,658, filed Feb. 18, 2016. Passage 85 (p85) was produced in a 5 L BioBLU single use bioreactor (Eppendorf, Hamburg, Germany) seeded with MARC-145 attached to HILLEX II microcarriers (Pall Corporation, Port Washington, N.Y.) in OPTI-MEM media (Life Technologies, Grand Island, N.Y.) supplemented with 2% Fetal Bovine Serum (Sigma, St. Louis, Mo.) and 50 ug/mL of Gentamycin (Life Technologies, Grand Island, N.Y.). The titer of the harvested p85 virus stock was 7.3 $log_{10}TCID_{50}$ as determined by the virus titration assay described in Example 3.

In a 1 L bottle, 19.7 mL of the 300 mM MBCD (Sigma, St. Louis, Mo.) stock solution was added to 300 mL of the SD 11-21 virus stock. The mixture was incubated at room temperature with constant mixing at 50 rpm for 24 hours. Following the 24 hour incubation an additional 9.8 mL of MBCD stock solution was added and the mixture incubated at room temperature with constant mixing at 50 rpm for an additional 24 hours. The final concentration of MBCD was 30 mM with a total of 48 hours of room temperature incubation. A mock inactivated virus stock was also prepared adding an equivalent amount of water in place of MBCD, incubation times and mixing were identical to the inactivated virus. The mock inactivated virus was used as a control for virus measurement assays. After treatment, the mock inactivated virus was present at 6.5 $log_{10}TCID_{50}$/mL, whereas no live virus was detected in MBCD-inactivated virus solution.

The virus stocks were stored at 4° C. until further use.

Vaccines were formulated to include a stabilizer and a preservative. OPTI-MEM® I Reduced Serum Medium was used as the blending diluent. Adjuvants included commercial formulations of MONTANIDE™ Gel 01 (Seppic) and MONTANIDE™ 1313 VG N PR (Seppic). The control product was a commercial preparation (Corning Cellgro, Mediatech Inc. of phosphate buffered saline (PBS). Vaccines without adjuvant contained delipated virus, 25% Stabililzer B, 25 μg/ml gentamycin as a preservative, and blending diluent. Vaccines with adjuvant contained 20% of the indicated adjuvant. Stabilizer B contained 2.5% D-mannitol (Sigma), 1.2% gelatin type A (Fisher, Pittsburgh, Pa.), 1% NZ amine casein hydrosylate (Sigma), 5% sucrose (Sigma), and 6.2% trehalose (Fisher) in ultra-pure water (Life Technologies) at pH 7.0-7.2.

Vaccination and Challenge

Each of the 60 pigs enrolled in the study were vaccinated on Day −35 pre-challenge. Pigs in T01-T05 were injected with their assigned treatment as a 1.0 mL intramuscular dose in the right side of the neck. Pigs in T06 were injected with 1.5 mL. Pigs in T01-T03 and T05 and T06 were vaccinated again 14 days later (−21 days pre-challenge) in the same manner. On 0 DPC, the challenge material was prepared by thawing the frozen aliquots of strain NADC-20 immediately prior to challenge. Titer was determined to be $1.26 \times 10^{5.0}$ $TCID_{50}$/ml after dilution in Minimum Essential Medium Eagle with Earle's salts and L-glutamine (MEM) from Mediatech, Inc. Each pig was physically restrained for the challenge with the head oriented upwards. A 3 mL non-luer lock syringe was used to deliver a 2 mL dose intranasally, with approximately 1 mL per nostril.

Results

At 14 DPC, animals were humanely euthanized per site procedures. Lungs were excised and scored by the Study Investigator who was blinded to treatment. Each of the seven pulmonary lobes was examined both visually and by palpation for gross characteristic lesions attributed to PRRSV. The amount of lesion/consolidation in each pulmonary lobe was scored as an actual value between 0 and 100% of the lobe. The score for each lobe was entered into a weighted formula to calculate the percentage of lung with lesions. Percentage of total lung with lesions was calculated according to the following formula: Percentage of total lung with lesions= {(0.10×left apical)+(0.10×left cardiac)+(0.25×left diaphragmatic)+(0.10×right apical)+(0.10×right cardiac)+(0.25× right diaphragmatic)+(0.10×intermediate)}.

In addition, the percentages of total lung with lesions were transformed using the arcsine square root, prior to further analysis. The transformed data were analyzed by a mixed linear model that included the fixed effect of treatment (the MIXED procedure in SAS) and the random effect of block.

Results of the statistical analysis of the lung lesion scores are summarized in Table 6. The main effect of treatment was statistically significant (P=0.0003). Comparisons with the control group (T01) indicated a significantly lower (P<0.05) percent lung involvement in the Gel 01 adjuvanted groups (T04 and T05). Also, non-adjuvanted vaccine administered twice and stored at 2-8° C. (T02) resulted in significantly lower (P<0.05) lesion scores than a similar group treated with a vaccine stored at −20° C. (T03).

TABLE 6

Mean Lung Lesion Score - Arcsine Transformed Percent Lung Involvement (main effect of treatment: P = 0.0003)

| Treatment Group | Estintate[1] | Standard Error | Mean[2] |
|---|---|---|---|
| T01 (Placebo) | 0.4760 | 0.1085 | 20.99 |
| T02 (no adjuvant, 2 doses) | 0.2761 | 0.1105 | 7.43 |
| T03 (Inactivated PRRS stored at −70° C.) | 0.6338 | 0.1085 | 35.07 |
| T04 (Gel 01 adjuvant, single dose) | 0.1678 | 0.1085 | 2.79* |

TABLE 6-continued

Mean Lung Lesion Score - Arcsine Transformed Percent Lung Involvement (main effect of treatment: P = 0.0003)

| Treatment Group | Estintate[1] | Standard Error | Mean[2] |
|---|---|---|---|
| T05 (Gel 01 adjuvant, 2 doses) | 0.2128 | 0.1141 | 4.46* |
| T06 (1313 adjuvant, 2 doses) | 0.3418 | 0.1085 | 11.24 |
| T02 v T03 | | | P-value = 0.0013 |
| T04 v T05 | | | P-value = 0.6692 |
| T02 v T05 | | | P-value = 0.5594 |

*T01 versus T04 and T05 significantly different at P < 0.05
[1]Untransformed means
[2]Back transformed means Blood samples for determination of viremia levels were collected on Days −35 and −21 pre-challenge. Additionally, blood samples for determination of viremia levels were collected at 0, 3, 7, 10 and 14 DPC. Samples were tested for the presence of PRRS viral nucleic acids using qRT-PCR techniques Serology and viremia data were transformed to $log_{10}$ units prior to analyses, given a non-normal distribution. The transformed values were analyzed using a repeated measures mixed model (the MIXED procedure). The statistical model included treatment, time, and treatment by time interaction as fixed effects. Block was included in the model as a random effect. If the treatment by time interaction was significant (P<0.05), the effects of within time treatment were evaluated. If the interaction was not significant, the main effect of treatment was assessed. Least squares means (back-transformed) and standard errors are presented.

The analysis of the viremia levels is summarized in Table 7. Viremia was not observed in any pig prior to PRRSV challenge confirming the vaccine virus was inactivated. Time points prior to challenge were excluded from the statistical analysis. Post-challenge, the treatment by day interaction was not significant (P=0.0974), thus the main effect of treatment was evaluated. The effect of treatment was significant (P=0.0107). Comparisons with the control group (T01) indicated significantly lower (P<0.05) levels in all vaccine groups that were adjuvanted (T04, T05 and T06). None of the pre-planned contrasts were statistically significant.

TABLE 7

Viremia - Geometric Means of PRRSV Genomic Copies/mL on 3, 7, 10 and 14 DPC ($log_{10}$ transformed) (main effect of treatment: P = 0.011; treatment by day interaction: P = 0.097)

| Treatment | Estimate[1] | Standard Error | Geometric Mean[2] |
|---|---|---|---|
| T01 (Placebo) | 6.2508 | 0.1149 | 1781506 |
| T02 (no adjuvant, 2 doses) | 5.9855 | 0.1211 | 967187 |
| T03 (Inactivated PRRS stored at −70° C.) | 6.2907 | 0.1149 | 1953141 |
| T04 (Gel 01 adjuvant, single dose) | 5.8753 | 0.1149 | 750379* |
| T05 (Gel 01 adjuvant, 2 doses) | 5.7720 | 0.1211 | 591543* |
| T06 (1313 adjuvant, 2 doses) | 5.8878 | 0.1149 | 772251* |
| T02 vs T03 | | | P-value = 0.0733 |
| T04 vs T05 | | | P-value = 0.5389 |
| T02 vs T05 | | | P-value = 0.2182 |

*T01 versus T04, T05, T06, significantly different at P < 0.05
[1]Untransformed log10 means
[2]Back transformed means

CONCLUSIONS

Vaccinating pigs with one or two doses of the MBCD inactivated, Gel 01 adjuvanted vaccine was effective in significantly reducing both lung lesions and viremia levels compared to the control group. Lung lesions were numerically reduced in pigs vaccinated with other MBCD inactivated vaccines (T02 and T06) stored at 2-8° C. Due to variation in lung lesion scores, these differences were not significant at the P<0.05 level. All MBCD vaccines that contained an adjuvant (MONTANIDE™ Gel 01 or 1313) significantly reduced viremia. In future studies, a larger sample size may be needed when the NADC-20 strain is utilized as the challenge material in order to detect meaningful biological differences in both lung lesions and viremia.

Storage temperature appears to have an impact on vaccine efficacy. Storing the vaccine at −20° C. had a negative effect on vaccine efficacy compared to vaccine stored at 2-8° C.

Adding an additional vaccination 14 days following the first did not further improve vaccine efficacy in pigs vaccinated with the MBCD inactivated vaccine adjuvanted with Gel 01.

The inclusion of the Gel 01 adjuvant to the MBCD inactivated vaccine did not affect vaccine efficacy.

MBCD inactivated vaccines were safe for growing swine as evidenced by no post-vaccination systemic reactions, no injection site lesions and only a transient (1 or 2 days) febrile response in the Seppic MONTANIDE™ Gel 01 adjuvanted groups following second vaccination.

What is claimed is:

1. A method of preparing an inactivated enveloped virus comprising:
   mixing a solution comprising an enveloped virus with a first methyl β-cyclodextrin (MBCD) solution to obtain a first mixture;
   incubating the first mixture for a first time period;
   mixing the enveloped virus from the first mixture with a second MBCD solution to obtain a second mixture; and
   incubating said second mixture for a second time period.

2. The method of claim 1 wherein a concentration of MBCD in the first mixture is at least 5 mM to about 100 mM.

3. The method of claim 1 wherein a concentration of MBCD in the first mixture is about 20 mM to about 40 mM.

4. The method of claim 1 wherein a concentration of MBCD in the second mixture is about 10 mM to about 100 mM.

5. The method of claim 1 wherein a concentration of MBCD in the second mixture is about 30 mM to about 50 mM.

6. The method of claim 1 wherein the first time period is about 15 minutes to about 24 hours.

7. The method of claim 1 wherein the first time period is about 4 hours to about 24 hours.

8. The method of claim 1 wherein the second time period is about 4 hours to about 48 hours.

9. The method of claim 1 wherein the second time period is about 24 hours, about 36 hours, or about 48 hours.

10. The method of claim 1 wherein a temperature of at least one of the first time period and the second time period is about 20° C. to about 25° C.

11. The method of claim 10 wherein the temperature is about 22° C. to about 24° C.

12. The method of claim 1 wherein the enveloped virus is isolated from the first mixture prior to the step of obtaining the second mixture.

13. The method of claim 1 wherein the enveloped virus is Porcine Reproductive and Respiratory Syndrome (PRRS) virus.

14. The method of claim 1 wherein at least one of the first time period and the second time period further comprises stirring of the first mixture and/or the second mixture.

15. A method of making a vaccine comprising:
   mixing a solution comprising an enveloped virus with a first methyl β-cyclodextrin (MBCD) solution containing a concentration of MBCD of at least 5 mM to about 100 mM to obtain a first mixture;
   incubating the first mixture for a first time period of about 15 minutes to about 24 hours;
   mixing the enveloped virus from the first mixture with a second MBCD solution containing a concentration of MBCD of at least 10 mM to about 100 mM to obtain a second mixture;
   incubating said second mixture for a second time period of about 4 hours to about 48 hours;
   isolating the enveloped virus; and
   combining the isolated enveloped virus with at least one of: an adjuvant, a stabilizer, a preservative, and a blending diluent;
   wherein a temperature of at least one of the first time period and the second time period is about 20° C. to about 25° C.

16. The method of claim 15 wherein the enveloped virus is Porcine Reproductive and Respiratory Syndrome (PRRS) virus.

* * * * *

UNITED STATES PATENT AND TRADEMARK OFFICE
CERTIFICATE OF CORRECTION

PATENT NO. : 10,420,831 B2
APPLICATION NO. : 16/060561
DATED : September 24, 2019
INVENTOR(S) : Stephen Wu et al.

Page 1 of 1

It is certified that error appears in the above-identified patent and that said Letters Patent is hereby corrected as shown below:

In the Specification

Column 1, Line 5:
Delete "Feb. 14, 2017"
Insert --Jan. 20, 2017--.

Signed and Sealed this
Thirty-first Day of December, 2019

Andrei Iancu
*Director of the United States Patent and Trademark Office*